United States Patent
Manabe et al.

(10) Patent No.: US 7,433,718 B2
(45) Date of Patent: Oct. 7, 2008

(54) MOBILE TERMINAL CAPABLE OF MEASURING A BIOLOGICAL SIGNAL

(75) Inventors: Hiroyuki Manabe, Yokosuka (JP);
Hirotaka Nakano, Musashino (JP);
Toshiaki Sugimura, Yokohama (JP);
Akira Hiraiwa, Yokohama (JP)

(73) Assignee: NTT DoCoMo, Inc., Tokyo (JP)

(*) Notice: Subject to any disclaimer, the term of this patent is extended or adjusted under 35 U.S.C. 154(b) by 162 days.

(21) Appl. No.: 10/461,354

(22) Filed: Jun. 16, 2003

(65) Prior Publication Data

US 2004/0034645 A1    Feb. 19, 2004

(30) Foreign Application Priority Data

Jun. 19, 2002    (JP)    ............... 2002-178900

(51) Int. Cl.
*H04M 1/00* (2006.01)
*H04M 11/00* (2006.01)

(52) U.S. Cl. ............... 455/575.1; 379/106.02

(58) Field of Classification Search ............... 455/575.1, 455/575.2, 575.3, 575.4, 575.5, 575.6, 575.7; 379/106.02; 600/300; 370/39, 38; 340/825.19
See application file for complete search history.

(56) References Cited

U.S. PATENT DOCUMENTS

| | | | | | |
|---|---|---|---|---|---|
| 3,978,847 | A | * | 9/1976 | Fehmi et al. | 600/545 |
| 4,596,256 | A | * | 6/1986 | Ascher et al. | 600/523 |
| 4,883,064 | A | * | 11/1989 | Olson et al. | 600/509 |
| 5,172,698 | A | * | 12/1992 | Stanko | 600/510 |
| 5,368,042 | A | * | 11/1994 | O'Neal et al. | 600/546 |
| 5,586,171 | A | * | 12/1996 | McAllister et al. | 379/88.02 |
| 6,270,466 | B1 | * | 8/2001 | Weinstein et al. | 600/590 |
| 6,327,495 | B1 | * | 12/2001 | Iwabuchi et al. | 600/547 |
| 6,353,396 | B1 | * | 3/2002 | Atlas | 340/693.9 |
| 6,396,416 | B1 | * | 5/2002 | Kuusela et al. | 340/870.28 |
| 6,485,416 | B1 | * | 11/2002 | Platt et al. | 600/300 |
| 6,546,232 | B1 | * | 4/2003 | Sack et al. | 455/90.1 |
| 6,727,197 | B1 | * | 4/2004 | Wilson et al. | 442/301 |
| 6,729,025 | B2 | * | 5/2004 | Farrell et al. | 29/854 |
| 2002/0077534 | A1 | * | 6/2002 | DuRousseau | 600/300 |
| 2002/0082007 | A1 | * | 6/2002 | Hoisko et al. | 455/426 |

(Continued)

FOREIGN PATENT DOCUMENTS

CA    2385232    *    5/2002

(Continued)

OTHER PUBLICATIONS

Noboru Sugie, et al., "A Speech Prosthesis Employing a Speech Synthesizer-Vowel Discrimination From Perioral Muscle Activities and Vowel Production", IEEE Transactions on Biomedical Engineering, vol. 32, No. 7, pp. 485-490.

*Primary Examiner*—William J Deane
(74) *Attorney, Agent, or Firm*—Oblon, Spivak, McClelland, Maier & Neustadt, P.C.

(57) ABSTRACT

A mobile terminal capable of measuring a biological signal is provided. The terminal comprises a terminal body; an electrode for human body earth or system reference, placed on an outer surface of the terminal body so as to be contactable with the skin of a user of the mobile terminal; and differential electrodes. The measured biological signals include an electromyography signal and an electroencephalogram signal. The differential electrodes can be external to the terminal body and be connected via lead lines to the terminal body.

3 Claims, 5 Drawing Sheets

U.S. PATENT DOCUMENTS

2002/0188216 A1* 12/2002 Kayyali et al. ............... 600/544
2005/0239493 A1* 10/2005 Batkin et al. ............. 455/550.1

FOREIGN PATENT DOCUMENTS

| | | |
|---|---|---|
| DE | 196 02 347 | 7/1997 |
| EP | 1 336 947 A2 | 8/2003 |
| EP | 1 345 210 A2 | 9/2003 |
| JP | 60-103935 | 6/1985 |
| JP | H06-12483 A | 1/1994 |
| JP | 7-181888 | 7/1995 |
| JP | H07-181888 A | 7/1995 |
| JP | 09-056685 | 3/1997 |
| JP | 2000-041962 | 2/2000 |
| JP | 2001346784 | * 12/2001 |
| WO | WO 98/38611 | 9/1998 |
| WO | WO 03/094720 | * 11/2003 |

* cited by examiner

MOBILE TERMINAL CAPABLE OF MEASURING A BIOLOGICAL SIGNAL

BACKGROUND OF THE INVENTION

1. Field of the Invention

The present invention generally relates to mobile terminals capable of measuring biological signals, and specifically relates to such a mobile terminal having an electrode for human body earth or system reference, placed on an outer surface of a terminal body.

2. Description of the Related Art

For example, when a handicapped person such as a person having no laryngopharynx or the oral part of pharynx after undergoing a laryngectomy tries to speak in vain, what the person is trying to speak can be determined by detecting perioral muscle activities. Then a speech synthesizer is driven to produce synthetic speech in place of the person's voice.

One good example of such research works is published in Noboru Sugie et. al., A Speech Prosthesis Employing a Speech Synthesizer—Vowel Discrimination from Perioral Muscle Activities and Vowel Production, IEEE transactions on Biomedical Engineering, Vol. 32, No. 7, pp 485-490, the entire contents of which are hereby incorporated by reference.

According to the research work, the movements of the mouth are picked up via three channels of electromyography with Ag—AgCl surface electrodes. After band-pass filtering of the electromyography, a thresholding operation is performed to reduce the noise component. Then the number of crossings of the threshold level is counted for each channel. Depending on the number of the count at each time interval, each muscle is assigned a 1 or 0 to designate an active or inactive state, respectively. Then a sequence of 3-bit numbers is fed to a finite automaton for vowel discrimination out of all the five basic Japanese vowels: /a/, /e/, /i/, /o/, and /u/. The output of the automaton is used to drive a speech synthesizer for vowel production.

One example of detecting electromyography signals to discriminate between Japanese vowels is shown in Japanese Patent Laid-open publication No. 7-181888, the entire contents of which are hereby incorporated by reference.

In this example, as shown in FIG. 5, a speech synthesizer 50 includes an electromyography (EMG) signal detecting unit 15 for detecting EMG signals caused by muscle movements due to speech activities, a syllable identifying unit 11 for generating identifying signals corresponding to desired syllables, a learning unit 13 for learning based on detected signals fed from the EMG signal detecting unit 15 and the identifying signals fed from the syllable identifying unit 11, a discrimination unit 17 for receiving input patterns fed from the EMG signal detecting unit 15 and discriminating and outputting sound syllable signals corresponding to the input patterns, a sound synthesizing unit 18 for synthesizing sound signals corresponding to the sound syllable signals fed from the discrimination unit 17 and converting the sound signals to sounds, a sound outputting unit 19 for outputting the sounds converted by the sound synthesizing unit 18.

The EMG signal detecting unit 15 has a plurality of skin surface electrodes 14 for detecting EMG signals corresponding to muscle movements, amplifiers 16 for amplifying the EMG signals detected by the skin surface electrodes 14, filters (not shown) for filtering out low and high frequency components from the amplified signals, and converters (not shown) for converting the filtered signals to power spectrums. Further, after the conversion to the frequency spectrums, the components separated by band can be processed in parallel, and therefore consonant discrimination becomes possible.

In addition to such medical use, there has recently been an increasing demand for human interfacing purposes to easily obtain and process human biological signals such as electromyography signals and electroencephalogram (brain wave) signals.

When obtaining biological signals such as EMG signals or electroencephalogram signals, operational amplifiers are normally used for reducing the external noise component. A plurality of electrodes are required to be attached to a human body in order to obtain EMG signals using the operational amplifiers. For example, in order to obtain one kind of EMG signal, at least three electrodes should be attached to a human body. That is, two electrodes for the operational amplifier and one electrode for body earth or system reference are needed. Some measurement devices require one electrode dedicated to the body earth and another electrode dedicated to the system reference. In this case, four electrodes are necessary for getting one kind of EMG signal.

Out of these electrodes, two electrodes for the operational amplifiers should be attached or patched on human skin in the gliding direction of muscle and at a place to be measured. On the other hand, the place where the electrode for the body earth or the system reference is attached is not specially limited, because the electrode is attached for the purpose of getting a reference potential for the operational amplifier or equalizing the operational amplifier ground potential with the human body.

In order to attach such electrodes, an operator should apply paste to the electrodes and then attach the electrodes to human skin, and fix them on the human body using tape. These processes need a lot of time and are troublesome. With regard to the body earth electrode or the system reference electrode, a band electrode can be wrapped around an upper extremity or an arm, or a lower extremity or a leg, or a clip electrode can be used by clipping it onto a lobule of auricle or an earlobe. Even if these simple electrodes are utilized, the electrode attaching operation is still necessary and troublesome.

Conventionally, the measurement of EMG signals and electroencephalogram signals has been mainly aimed at medical clinical examination or therapy, and therefore the prior art electrodes were assumed to be used only in examination rooms or operating rooms. Therefore, where the biological signals such as EMG signal or electroencephalogram are utilized as human interfacing means, it is necessary to make the electrode attaching operation easier and simpler as much as possible to reduce user's workload. And even when the biological signals such as the EMG signals or electroencephalogram signals are used for the purposed of examination or therapy, it is much better to make the electrode attaching operation easier or simpler.

As mentioned above, in order to obtain biological signals such as EMG signals or electroencephalogram signals, it is necessary to attach two kinds of electrodes: differential electrodes, and a body earth or system reference electrode. The place where the differential electrodes should be attached is limited to areas to be measured. The place where the body earth or system reference electrode should be attached is not specially limited. Therefore, the differential electrodes have limited places to be attached, and therefore should be attached to the most appropriate portion using the best attaching method. The differential electrode is therefore usually not necessarily attached in a simple manner.

On the other hand, the body earth or the system reference electrode without limitation to the attaching places can be attached anywhere in a predetermined certain area. Therefore, if there would exist one way to attach the body earth or the system reference electrode to a certain area of a human body in a simple manner, then it would be possible to avoid trouble when attaching the electrode. Specific examples for simply attaching are the above mentioned band electrode or clip electrode.

When the biological signals such as EMG signals or electroencephalogram signals are measured for the purpose of human interface use, the utility value of the biological signal measurement would be significantly increased if such measurement could be performed without any limitation in its measuring place, and the measured results could be identified and transmitted to a remote area through wired or wireless communication.

In order to realize the above mentioned improvement, it is desired to utilize a mobile terminal such as a mobile phone or a personal digital assistant (PDA) for obtaining biological signals such as EMG signals or electroencephalogram signals. When using a mobile terminal such as a mobile phone or a PDA to measure biological signals such as EMG signals or electroencephalogram signals, it is especially important to be able to simply and easily attach an electrode for body earth or system reference to a human body.

SUMMARY OF THE INVENTION

Accordingly, it is one object of the present invention to provide a mobile terminal such as a mobile phone or a PDA that is capable of measuring a biological signal, with an electrode for human body earth or system reference having no limitation in place to be attached.

Another and more specific object of the present invention is to provide a mobile terminal capable of measuring a biological signal, comprising: a terminal body; an electrode for human body earth or system reference, placed on an outer surface of the terminal body so as to be contactable by the skin of a user of the mobile terminal; and differential electrodes.

The biological signal includes an electromyography (EMG) signal and an electroencephalogram signal or brain wave in a non-limiting sense. The mobile terminal includes a mobile phone, a personal digital assistance (PDA), a head mount display (HMD), and a wrist watch type terminal, and any other small mobile terminal that can measure the biological signal. The mobile terminal may include a function for analyzing or transmitting the biological signal. While holding a mobile terminal with a hand, or wearing it on ears, biological signals such as an EMG signal and a brain wave signal can be measured, and stored or transmitted via wired or wireless communication. It is important here that the mobile terminal necessarily contacts the human skin; a mobile phone and a PDA contact the hand, and an HMD contacts the forehead or temples.

In this manner, when measuring an EMG signal or an electroencephalogram signal using a mobile terminal according to the present invention, in which an electrode for human body earth or system reference is placed on an outer surface of the terminal body, it is possible to easily obtain body earth or system reference potential without specially attaching an electrode to the human body.

FIG. 1 shows a basic concept of the present invention. A mobile terminal having electrodes includes a mobile phone, a PDA, an HMD, a wrist watch terminal and other varieties of terminals as mentioned above, and a rectangular 10 in FIG. 1 represents all of such terminals. The mobile terminal 10 is provided with an electrode 12 as shown in FIG. 1. The electrode 12 is placed on an outer surface of the mobile terminal 10, at a portion that may contact human skin. The mobile terminal 10 is further provided with a plurality of electrodes 14 for operational amplifiers.

The electrode 12 placed at a portion that may contact human skin may function as a body earth electrode or a system reference electrode. Accordingly, a user only has to hold or wear the mobile terminal 10 to measure a body earth or system reference potential, without need to specially attach another body earth or system reference electrode. By attaching remaining differential electrodes at desired portions, it becomes possible to easily and quickly measure biological signals or biometrics signals such as an EMG signal or an electroencephalogram signal. In this manner, troublesome operations for attaching an electrode for body earth or system reference can be eliminated.

Features and advantages of the present invention will be set forth in the description that follows, and in part will become apparent from the description and the accompanying drawings, or may be learned by practice of the invention according to the teachings provided in the description. Objects as well as other features and advantages of the present invention will be realized and attained by an apparatus particularly pointed out in the specification in such full, clear, concise, and exact terms as to enable a person having ordinary skill in the art to practice the invention.

DESCRIPTION OF THE PREFERRED EMBODIMENTS

In the following, embodiments of the present invention will be described with reference to the accompanying drawings.

Figure 1:
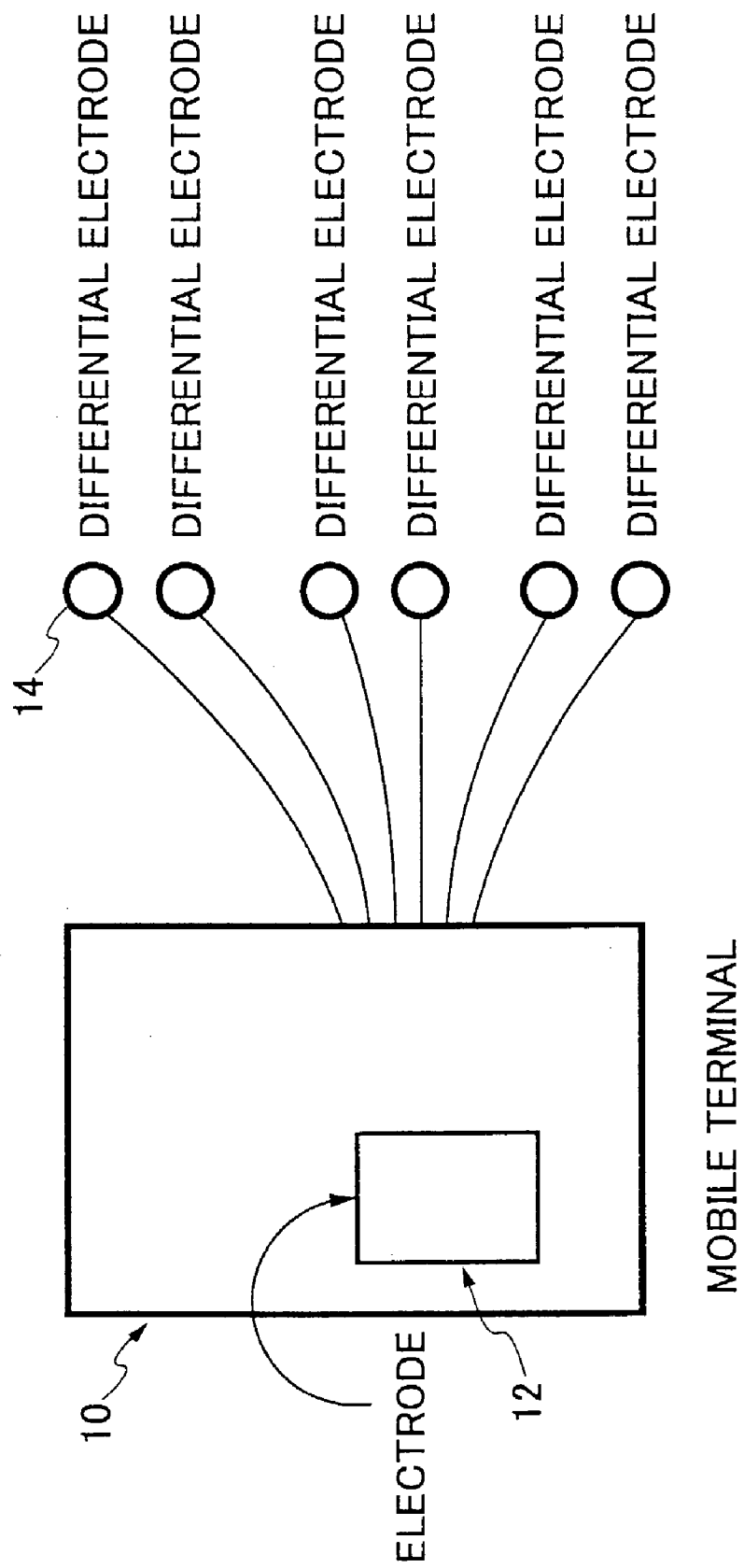
FIG. 1 shows a basic concept of the present invention.
Figure 2:
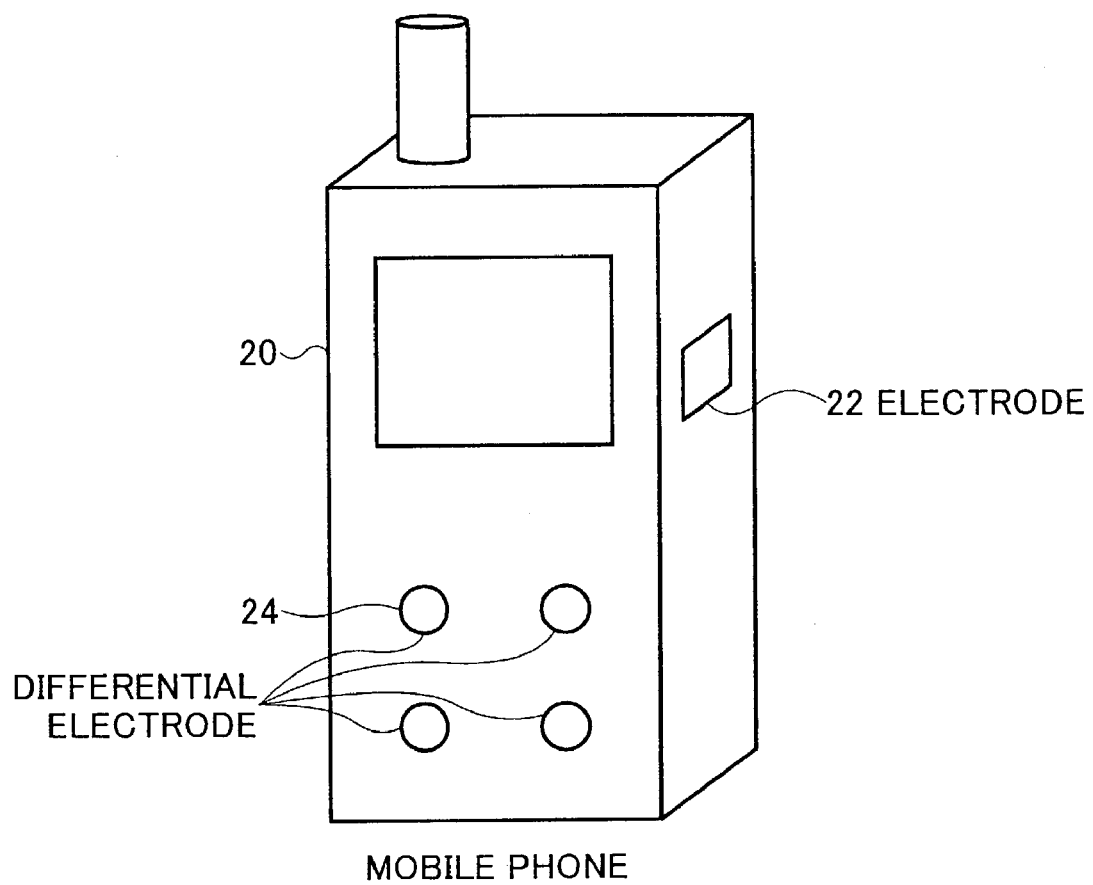
FIG. 2 is a schematic view of a mobile phone according to a first embodiment of the present invention.

FIG. 2 schematically shows a mobile phone 20 as a mobile terminal and its electrode configuration according to one embodiment of the present invention. The mobile phone 20 has an electrode 22 for body earth or system reference on a side surface thereof. A plurality of electrodes 24 for operational amplifiers are placed on a front surface of the mobile phone 20. While a user holds the mobile phone 20 to make a phone call, the mobile phone 20 maintains contact with a the skin on a hand and the face of a user. For example, a side surface of the mobile phone 20 contacts fingers, the back surface of the mobile phone 20 contacts a palm, or the front surface of the mobile phone 20 contacts an ear or a cheek. The contacting potions vary and are dependent on the shape of the mobile phone 20. A candy bar type mobile phone and clam shell type mobile phone have different contacting portions. Whatever shape mobile phones have, the mobile phones make contact with human skin. Therefore, an electrode for body earth or system reference can be placed at an appropriated portion of the mobile phone.

In the first embodiment shown in FIG. 2, the electrodes 24 for operational amplifiers are also placed on the mobile phone 20. These differential electrodes 24 need to be placed so as to make contact with a desired place of the human body to be measured. For example, when the mobile phone 20 is in contact with a cheek and the cheek is a place to be measured, the arrangement of the electrodes 24 as shown in FIG. 2 is appropriate.

The electrodes 24 for operational amplifiers are not necessarily placed on the mobile phone itself; they can be external to the mobile phone 20 and remotely connected to the mobile phone 20 via lead lines (not shown).

Figure 3:
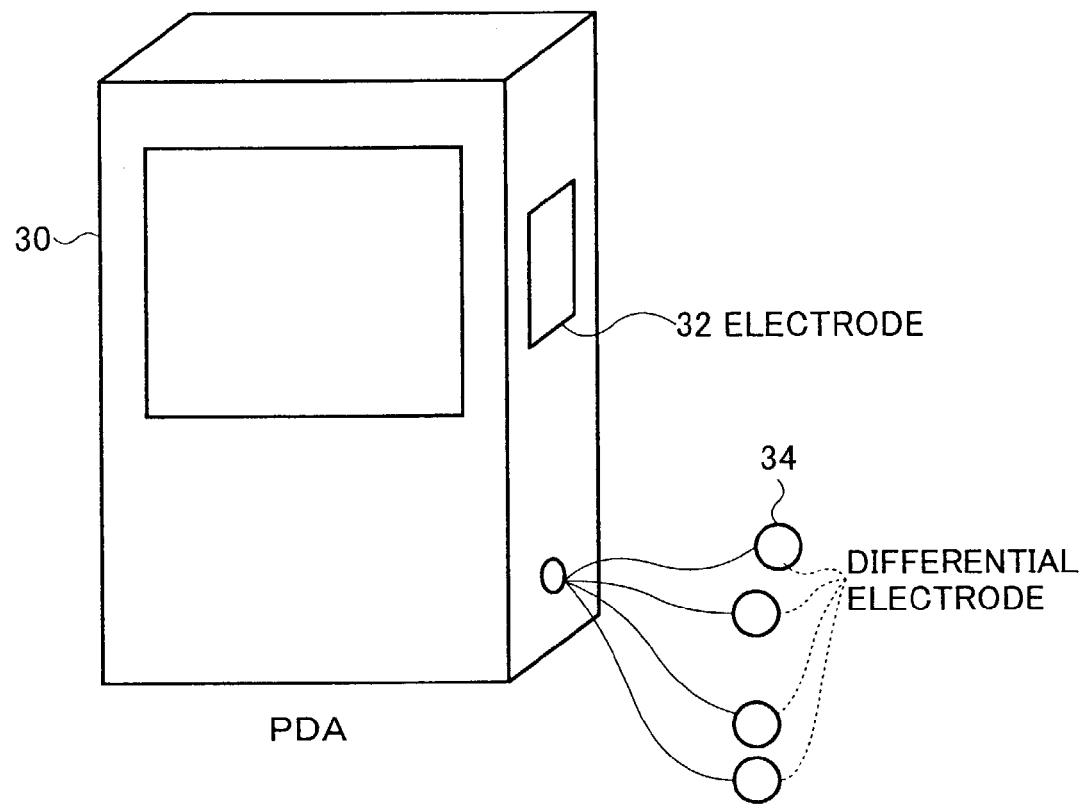
FIG. 3 is a schematic view of a PDA according a second embodiment of the present invention.

FIG. 3 schematically shows a personal digital assistant (PDA) 30 as a mobile terminal and its electrode configuration according a second embodiment of the present invention. The PDA 30 shown in FIG. 3 has an electrode 32 for body earth or system reference on a side surface thereof. A plurality of electrodes 34 for operational amplifiers are placed external to the mobile terminal 30 and remotely connected to the mobile terminal 30 via lead lines. These electrodes 34 may have Ag—AgCl surfaces.

While a PDA user holds the PDA 30 with a hand, the PDA 30 maintains contact with the hand, fingers or an arm of the user, as similar to the mobile phone 20 shown in FIG. 2. The contacting portions vary and are dependent on the shape of the PDA 30. Whatever shape PDAs have, the PDAs make contact with human skin without exception. Therefore, an electrode for body earth or system reference can be placed at an appropriated portion of the PDA 30.

The differential electrodes 34 can be attached to appropriate portions of the skin of a user to measure biological signals.

Alternatively, the differential electrodes 34 may be placed on the PDA surface, if a human skin portion that makes contact with the PDA is to be measured.

Figure 4:
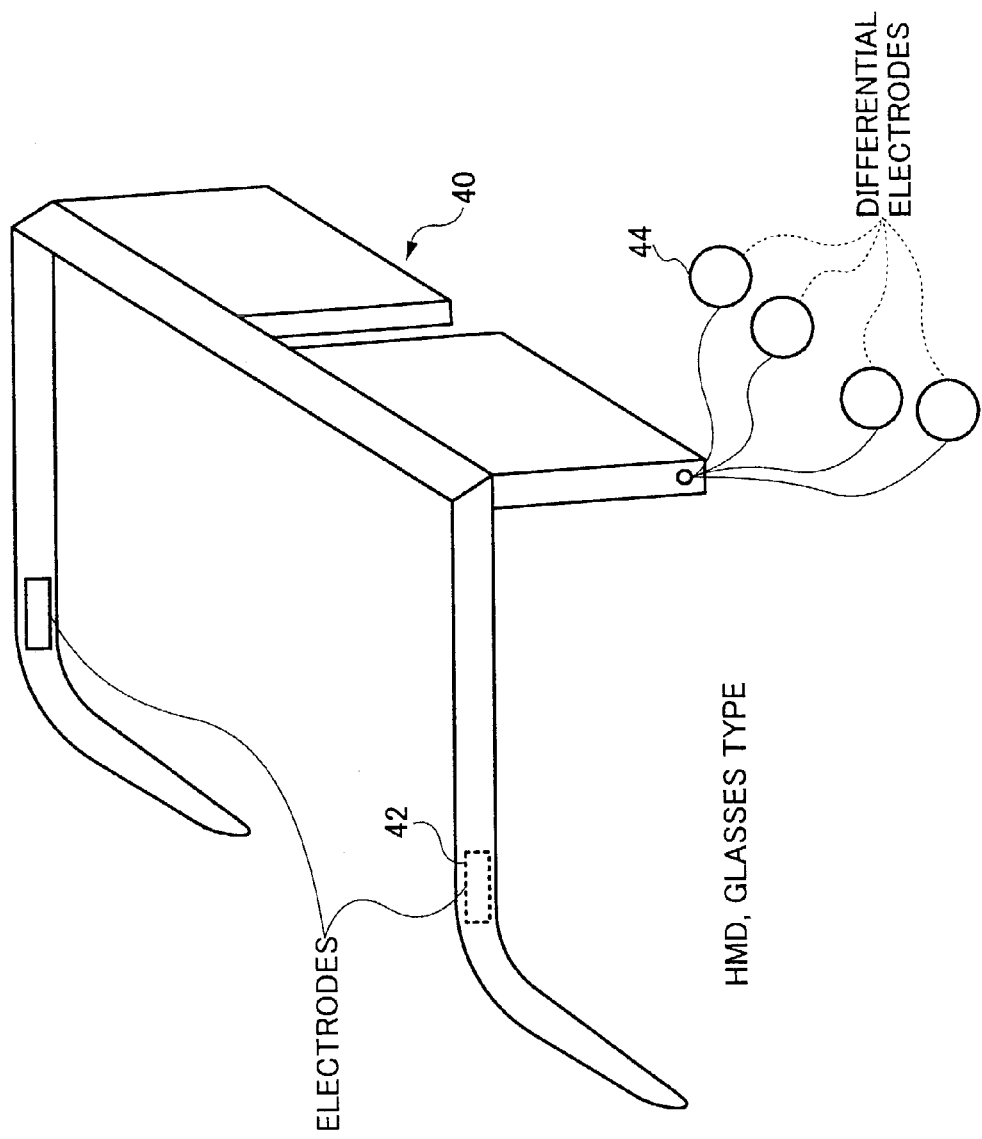
FIG. 4 is a schematic view of an HMD or glasses according to a third embodiment of the present invention.
Figure 5:
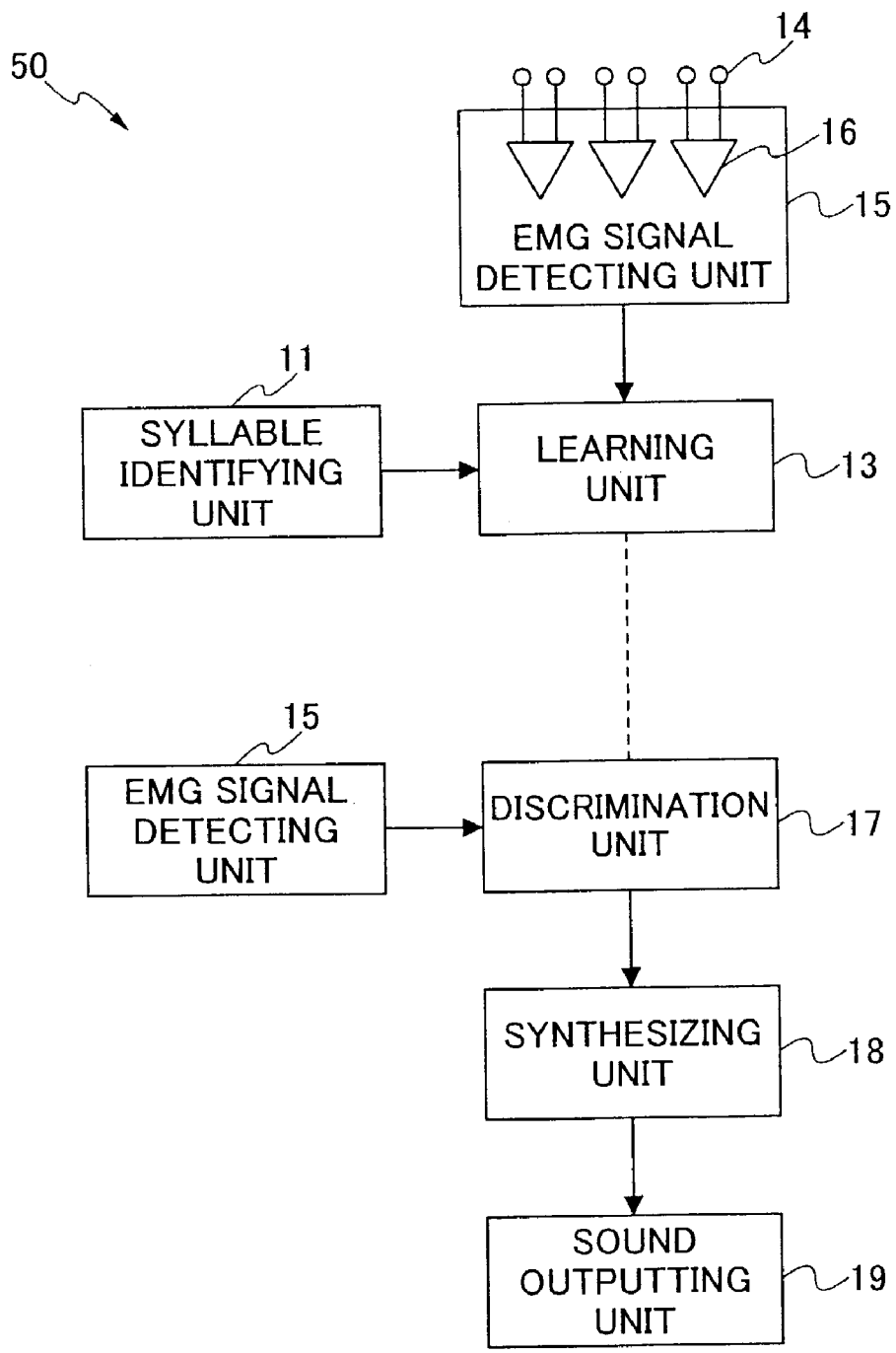
FIG. 5 is a schematic block diagram of a speech synthesizer.

FIG. 4 schematically shows an HMD or glasses 40 as a mobile terminal and its/their electrode configuration according to a third embodiment of the present invention. In the HMD 40 shown in FIG. 4, electrodes 42 for body earth or system reference can be placed at temples of the HMD 40 and can be in contact with the temples of a user.

Electrodes 44 for operational amplifiers can be remotely arranged and connected to the HMD 40 via lead lines. Alternatively, the electrodes 44 can be placed on the HMD 40 itself, if it is desired to measure a skin portion of the user that contacts the HMD 40.

In a case where a headset (not shown) is utilized as a mobile terminal, both a body earth or system reference electrode and differential electrodes can be placed on the headset to measure an electroencephalogram or a brain wave of a user.

Although the above embodiments with reference to FIGS. 2, 3 and 4 are explained using a mobile phone, a PDA, an HMD and glasses as a mobile terminal, the present invention is not limited to these examples. "Mobile terminal" referred to in this Description and Claims includes a variety of terminals having various shapes or functions in addition to the above mentioned terminals. The present invention can be applied to, for example, a wrist watch terminal, a finger ring terminal, a necklace terminal and any other terminal that can contact human skin.

In a mobile phone or a PDA according to the embodiments of the present invention, a body earth or system reference electrode can be easily placed without any trouble at an appropriate portion of a user's skin, and biological signals such as an EMG signal or a brain wave signal can be measured anywhere.

The mobile phone according to the first embodiment of the present invention is useful for a handicapped person who has a speaking problem, and useful when used in a place where speaking audibly is inhibited, because perioral muscle activities can be identified to discriminate between the sounds the user wants to speak.

In a case where a mobile terminal having communication function is utilized, it is possible to transmit measured biological signals to external devices, and realize broader applications in addition to medial use and human interfacing use.

The present application is based on Japanese priority application No. 2002-178900 filed on Jun. 19, 2002 with the Japanese Patent Office, the entire contents of which are hereby incorporated by reference.

What is claimed is:

1. A mobile phone capable of measuring a biological signal, comprising:
    a terminal body;
    an electrode for human body earth or system reference, placed on an outer surface of the terminal body so as to be contactable with a skin of a hand of a user of the mobile phone when said hand holds the mobile phone; and
    a plurality of differential electrodes configured to measure a biological signal and configured for use as a human interface, and placed on an outer surface of the mobile phone so as to be contactable with the skin on a cheek of the user;
    wherein the mobile phone is configured to measure the electromyography signal on the cheek of the user, said user having a speaking problem, or a person under a situation in which speaking audibly is inhibited so that the person can use the mobile phone.

2. The mobile phone as claimed in claim 1, wherein the biological signal is an electromyography signal or an electroencephalogram signal.

3. The mobile phone as claimed in claim 1, wherein the differential electrodes are placed on the outer surface of the mobile phone so that said differential electrodes are contactable with appropriate portions of the skin on the face of the user for measuring the biological signal.

* * * * *